(12) United States Patent
Grenon

(10) Patent No.: US 7,618,090 B2
(45) Date of Patent: Nov. 17, 2009

(54) ABDOMINAL SUPPORT SWIVEL CHAIR

(75) Inventor: Daniel Grenon, Soral-Tracy (CA)

(73) Assignee: Distribution Gablex Inc., Sorel-Tracy (CA)

( * ) Notice: Subject to any disclaimer, the term of this patent is extended or adjusted under 35 U.S.C. 154(b) by 0 days.

(21) Appl. No.: 11/634,123

(22) Filed: Dec. 6, 2006

(65) Prior Publication Data

US 2007/0246990 A1 Oct. 25, 2007

Related U.S. Application Data

(63) Continuation of application No. PCT/CA2006/000642, filed on Apr. 20, 2006.

(51) Int. Cl.
A47C 7/02 (2006.01)

(52) U.S. Cl. .................. 297/195.11; 297/353; 297/383; 297/374; 297/423.11; 297/423.12; 297/423.13; 297/487; 297/488; 248/188.7

(58) Field of Classification Search ............ 297/195.11, 297/374, 344.21, 383, 353, 423.13, 423.11, 297/423.12, 487, 488; 248/188.7
See application file for complete search history.

(56) References Cited

U.S. PATENT DOCUMENTS

| | | | | | |
|---|---|---|---|---|---|
| 693,685 | A | * | 2/1902 | Case ........................ | 297/353 X |
| 1,025,953 | A | * | 5/1912 | Hallen ......................... | 297/487 |
| 1,184,801 | A | * | 5/1916 | Watkins .................... | 297/353 X |
| 1,357,826 | A | * | 11/1920 | Shaw ...................... | 297/383 X |
| 1,719,929 | A | * | 7/1929 | Ferris .......................... | 297/353 |
| 1,938,226 | A | * | 12/1933 | Sims et. al. .............. | 297/353 X |
| 2,056,965 | A | * | 10/1936 | Herold .................... | 297/353 X |
| 2,356,507 | A | * | 8/1944 | Cramer .................... | 297/353 X |
| 2,400,630 | A | * | 5/1946 | Cramer et al. .......... | 297/383 X |
| 2,568,988 | A | * | 9/1951 | Childs ..................... | 297/353 X |
| 2,595,901 | A | * | 5/1952 | Sperring .................. | 297/383 X |
| 2,662,586 | A | * | 12/1953 | Cramer .................... | 297/383 X |
| 2,956,619 | A | * | 10/1960 | Scherer ................... | 297/383 X |
| 2,973,031 | A | * | 2/1961 | Cramer, Jr .................. | 297/383 |
| 2,988,398 | A | * | 6/1961 | Hamilton ..................... | 297/383 |
| 3,029,106 | A | * | 4/1962 | Mcguire ..................... | 297/311 |
| 3,041,636 | A | * | 7/1962 | Twedt ........................ | 297/5 X |
| 3,145,053 | A | * | 8/1964 | Thompson et. al. ......... | 297/383 |
| 3,338,626 | A | * | 8/1967 | Hamilton ..................... | 297/115 |
| 3,477,673 | A | * | 11/1969 | Bereday .................. | 297/353 X |
| 3,720,443 | A | * | 3/1973 | Mourgue ..................... | 297/383 |
| 3,754,787 | A | * | 8/1973 | Garber ..................... | 297/195.1 |

(Continued)

*Primary Examiner*—Rodney B White
*Assistant Examiner*—Kaitlin A. Wilson
(74) *Attorney, Agent, or Firm*—Ogilvy Renault LLP

(57) ABSTRACT

An abdominal support swivel chair is comprised of a support base with a plurality of leg arms having casters and radiating about the base frame in a common horizontal plane. An adjustable center post assembly extends vertically from the center of the support base and along a central vertical axis. A seat is secured to a frame connected at a top end of the center post. The seat has a rear buttocks support section and a central narrow frontal projecting section merging therewith through opposed side thigh cavities. An abdominal support pad is secured to an adjustable support arm connected to the saddle frame. The support arm has an upper securing end section adapted for securement of the abdominal support pad and to position same inclined forwardly. The adjustable support arm extends forwardly of the frontal projecting section and aligned therewith and has an adjustable connecting mechanism to position the abdominal support pad for the comfort of a user person above the frontal projecting section.

18 Claims, 8 Drawing Sheets

U.S. PATENT DOCUMENTS

| | | | |
|---|---|---|---|
| 3,837,704 A * | 9/1974 | Bauer | 297/353 X |
| 3,837,705 A * | 9/1974 | Marraccini | 297/353 |
| 4,099,774 A * | 7/1978 | Sandham | 297/353 X |
| 4,452,487 A * | 6/1984 | Plowman | 297/411.35 |
| 4,552,404 A * | 11/1985 | Congleton | 297/330 |
| 4,607,882 A * | 8/1986 | Opsvik | 297/195.11 |
| 4,650,249 A * | 3/1987 | Serber | 297/423.11 X |
| 4,790,600 A * | 12/1988 | Behringer | 297/337 |
| 4,832,407 A * | 5/1989 | Serber | 297/423.12 |
| 4,858,991 A * | 8/1989 | Boyesen | 297/487 X |
| 5,035,466 A * | 7/1991 | Mathews et al. | 297/353 X |
| 5,054,857 A * | 10/1991 | Kvalheim | 297/423.12 X |
| 5,066,069 A * | 11/1991 | DeGelder | 297/374 |
| 5,152,581 A * | 10/1992 | Norsworthy | 297/423.28 |
| 5,261,727 A * | 11/1993 | Klaebel | 297/423.13 |
| 5,295,728 A * | 3/1994 | Schaevitz | 297/423.12 X |
| 5,425,566 A * | 6/1995 | Buchacz | 297/353 X |
| 5,476,306 A * | 12/1995 | Golynsky | 297/362.12 |
| 5,490,716 A * | 2/1996 | Naughton | 297/423.12 |
| 5,516,197 A * | 5/1996 | Condos | 297/383 X |
| 5,542,746 A * | 8/1996 | Bujaryn | 297/423.12 |
| 5,560,682 A * | 10/1996 | Brown | 297/374 |
| 5,887,948 A * | 3/1999 | Hannes | 297/411.35 |
| 6,059,239 A * | 5/2000 | Wheeler | 248/188.7 |
| 6,123,390 A * | 9/2000 | Greenwald | 297/452.32 |
| 6,394,547 B1 * | 5/2002 | Vik | 297/353 X |
| 6,619,747 B2 * | 9/2003 | Ko et al. | 297/423.12 |
| 6,877,812 B2 * | 4/2005 | Congleton et al. | 297/353 |
| 6,921,135 B2 * | 7/2005 | Ellis et al. | 297/353 X |
| 7,093,900 B1 * | 8/2006 | Schon | 297/344.11 |
| 7,104,606 B2 * | 9/2006 | Congleton et al. | 297/353 |
| 7,234,768 B2 * | 6/2007 | Manning | 297/383 X |
| 7,261,368 B1 * | 8/2007 | Clausnitzer | 297/423.12 X |
| 2003/0034678 A1 * | 2/2003 | Farre | 297/195.11 |
| 2007/0052275 A1 * | 3/2007 | Ghilzai | 297/423.12 |

* cited by examiner

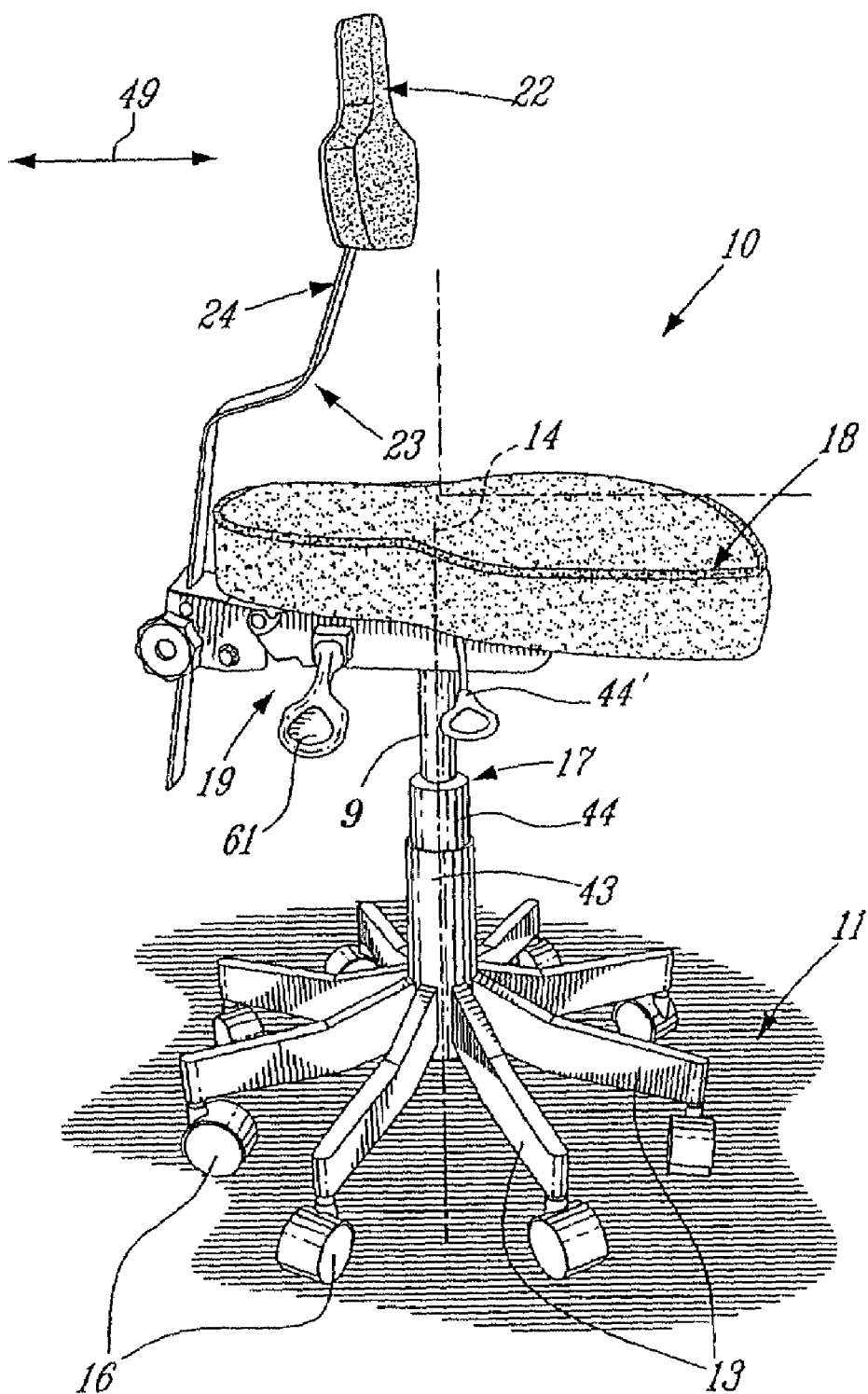
FIG_1

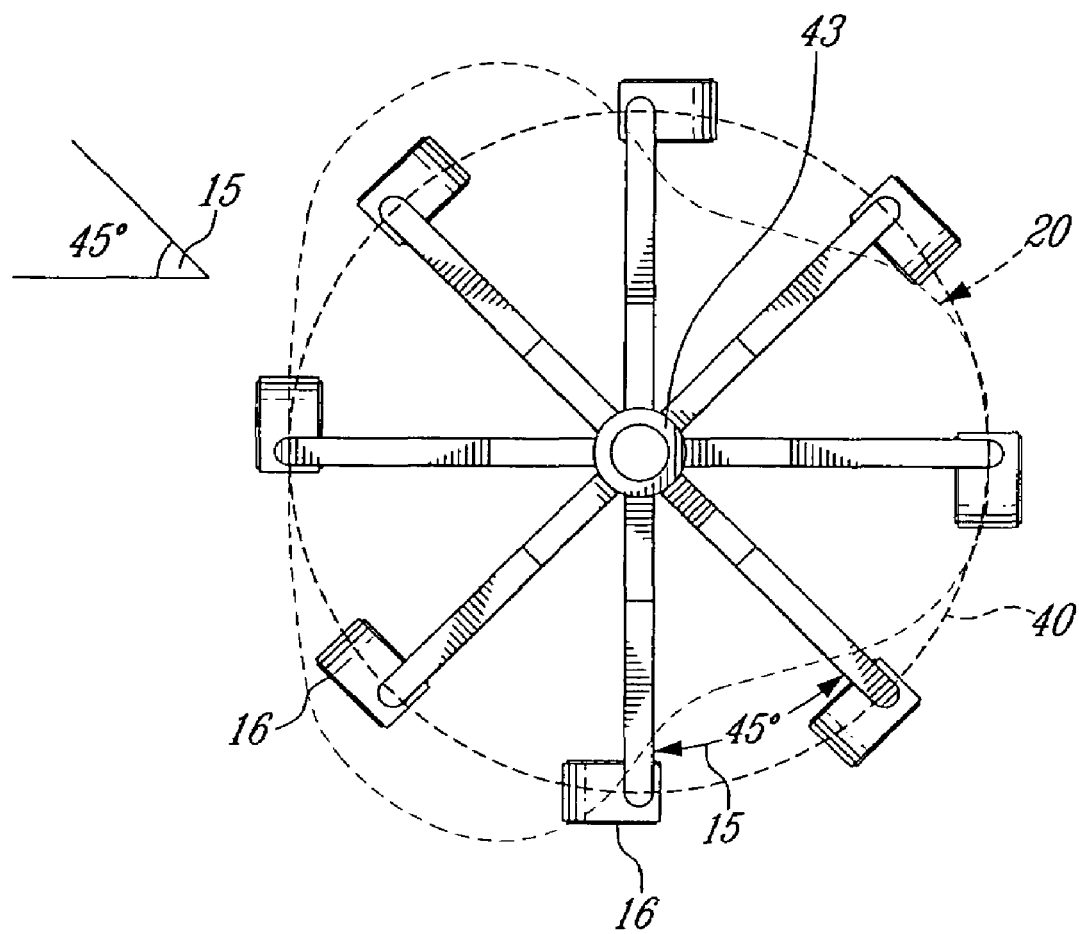
FIG_3

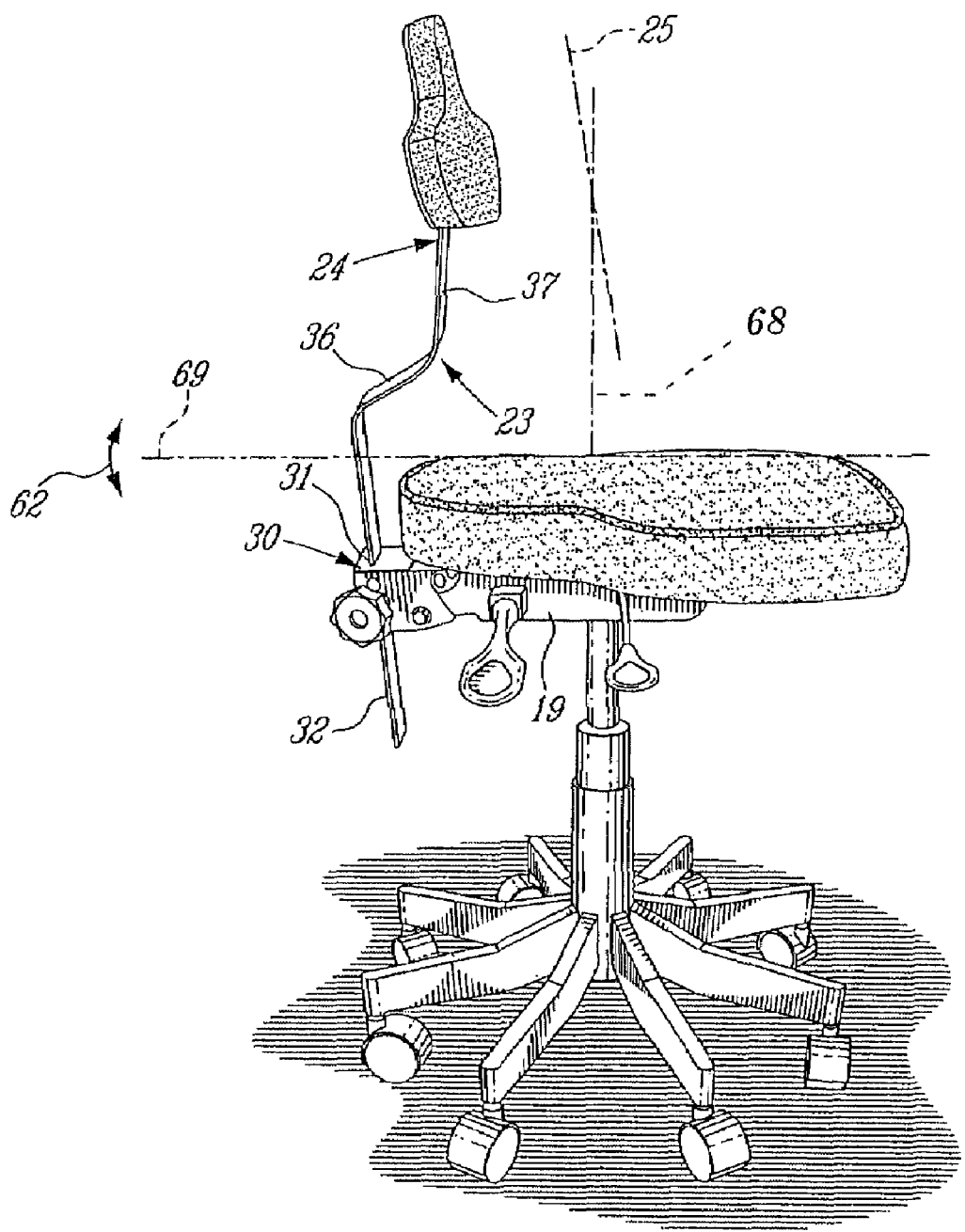
FIG._4A

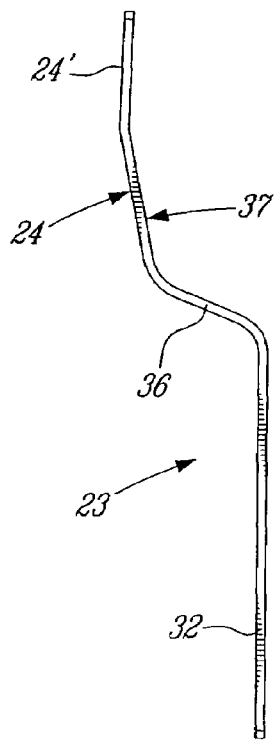
FIG_4B
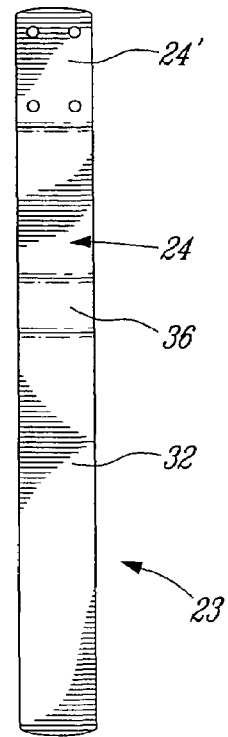
FIG_4C
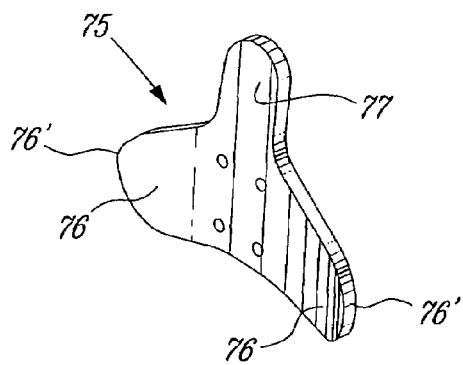
FIG_4D
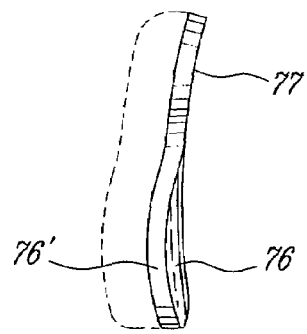
FIG_4E

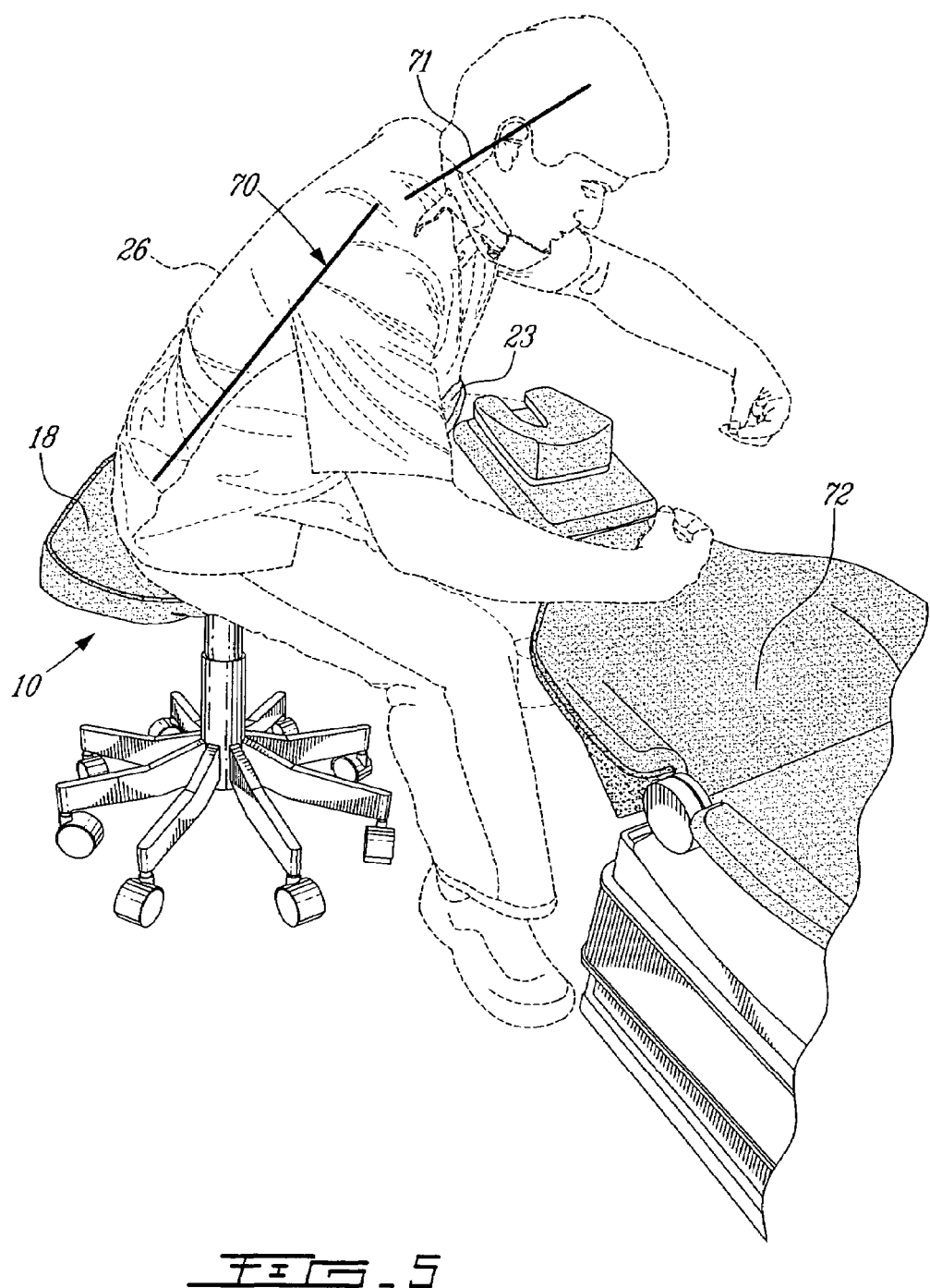
FIG_5

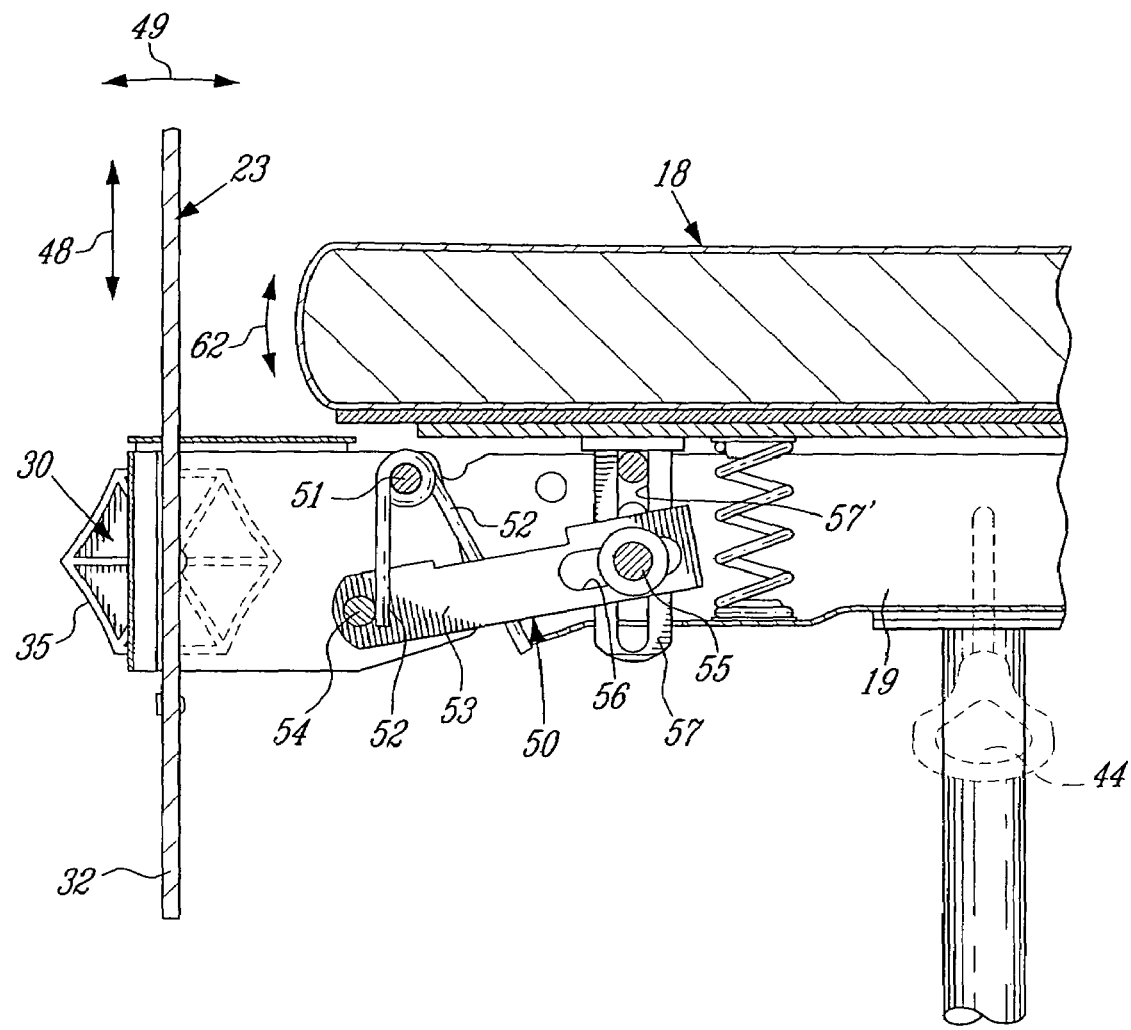
FIG_8

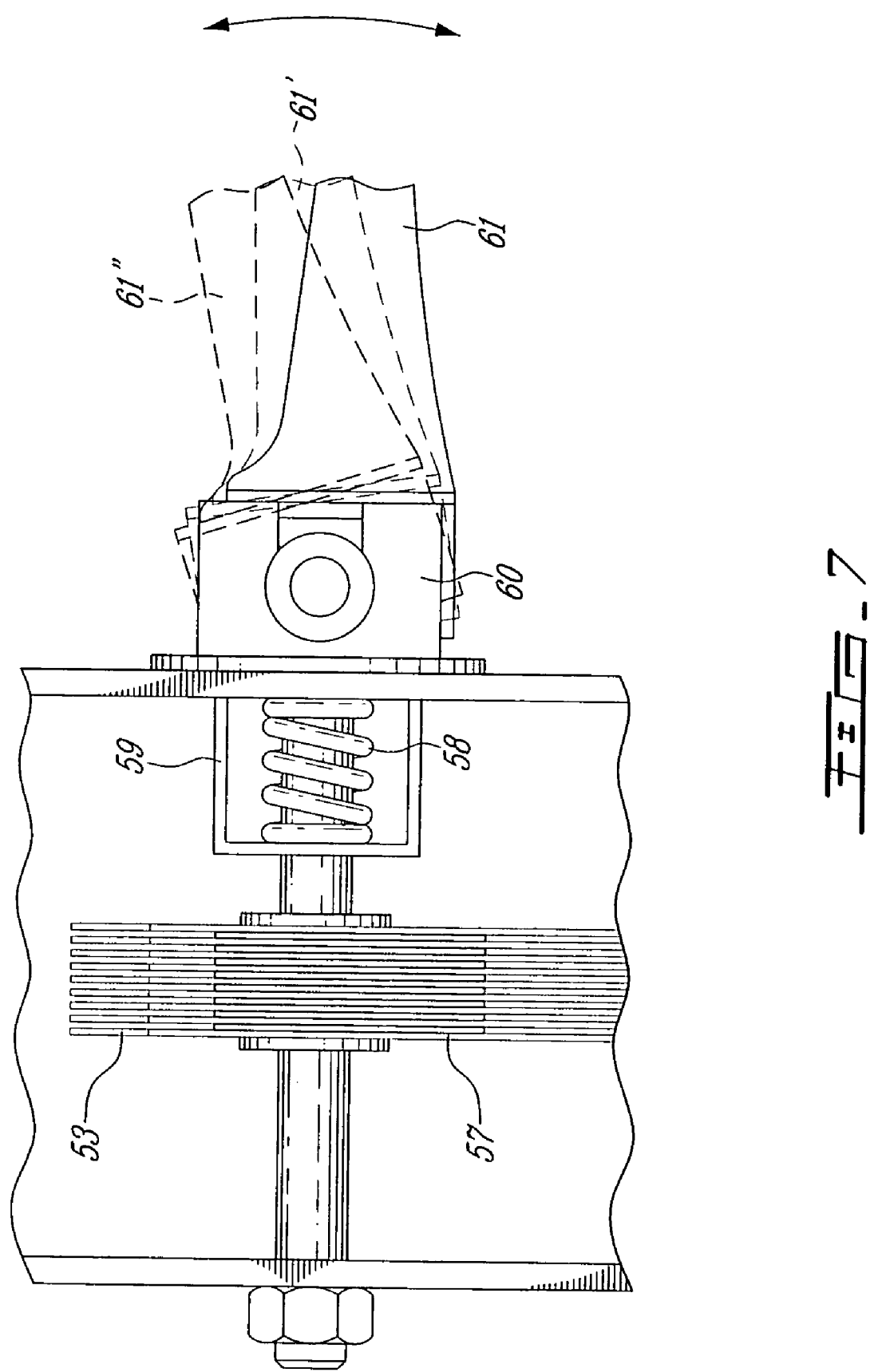

ABDOMINAL SUPPORT SWIVEL CHAIR

RELATED APPLICATION

This application is a continuation of International Patent Application No. PCT/CA2006/000642 filed on Apr. 20, 2006, which is herein incorporated by reference.

TECHNICAL FIELD

The present invention relates to an abdominal support swivel chair and particularly, but not exclusively, to a chair for use by dentists or other persons who require working with their hands while their back is forwardly inclined on a seat surface.

BACKGROUND ART

Chairs having supports to engage the chest of a user person, such as a dentist, hygienist, surgeon, etc., is known in the art and such chair or seating apparatus are, for example, described in U.S. Pat. Nos. 3,754,787; 4,832,407 and 6,619,747. However, such support chair assemblies still provide disadvantages including freedom of movement of the user person when seated on the chair and performing a work task forwardly of the seating surface. The seat of the chair also needs to provide comfort to the user person particularly when working long hours in a forwardly inclined seated or crouched position. Such chairs also need to provide free rotational movement of the user person when seated on the chair while preventing the chair from overturning and causing injury.

In recent years a study was effected by the ASSTSAS Association and dealing with the risk factors to dentists and dental assistants that work in dental clinics and particularly the problems that such people develop at the musculo-skeleton level due to their work habits. The study revealed that the chairs that these people are using hinder the blood circulation in the legs and cause muscular and spinal back and neck problems due to the fact that the back and neck are inclined forwardly when working on a patient as the back is not properly supported on the chair. When working in such awkward positions for long periods of time all of the tension is directed to the back of the working person which supports the inclined chest and head of the dentist or dental assistant. To counteract the stress on the back, the working person will brace his legs in such a way as to liberate this tension but this has led to the cause of other problems, such as pinching the sciatic nerve. The study effected by the Association of Dental Surgeons and Dentists of the Province of Quebec, Canada (ACDQ) reveals that these people, after working long hours and for several years, develop lower back problems, problems in the neck area and in the shoulders. The more frequent pathologies are tendonitis, bursitis, degeneration of the lumbar disc and the discs in the neck region as well as causing spinal-disc compression and disc hernias, to mention a few. Studies have also shown that the chairs used by dentists often obstruct the dentist's arm movements causing the dentist to assume awkward postures when performing his job function. The study has also shown that the average work life cycle of a dental assistant is about seven (7) years and this is due particularly to all these muscular problems that these people develop due to their work related activities. Also, this type of bad posture causes fatigue and the productivity of the individual is diminished.

The study by ASSTSAS also has resulted in various recommendations concerning the use of proper equipment in an attempt to alleviate all of these muscular and spinal problems. Reference is therefore made to this publication for background art as well as the other studies referred to therein such as studies effected by the American Public Health Association, Herbert 1998, pages 375 to 396. All of the proposed devices have not proven satisfactory to overcome the above-mentioned problems.

DISCLOSURE OF INVENTION

It is a feature of the present invention to provide an abdominal support swivel chair which substantially overcomes all of the above-mentioned disadvantages of the prior art.

According to the above feature, from a broad aspect, the present invention provides an abdominal support swivel chair which is comprised of a support base having displaceable support means for displacing the chair on a support surface. An adjustable center post assembly extends vertically from a center of the support base along a central vertical axis of the support base. A seat is secured to a seat frame secured to a top end of the adjustable center post. An abdominal support pad is secured to an adjustable support arm connected to the seat frame. The support arm has an upper securing end section adapted for securement of the abdominal support pad. The adjustable support arm is connected forwardly of the seat frame and aligned therewith. Adjustable connecting means positions the abdominal support pad at a desired vertical position and a forwardly inclined position for the comfort of a user person. The abdominal support pad is dimensioned to provide freedom of arm movement to a user person and supporting a central area of the abdomen of a user person.

BRIEF DESCRIPTION OF THE DRAWINGS

A preferred embodiment of the present invention will now be described with reference to the accompanying drawings in which:

FIG. 1 is a perspective view of an abdominal support swivel chair constructed in accordance with the present invention;

FIG. 3 is a top view illustrating the construction of the support base and its spider-like legs;

FIG. 4A is a perspective view showing the abdominal support pad secured elevated by a support arm in front of the saddle seat;

FIG. 4B is a side view of the support arm;

FIG. 4C is a plan view of the support arm;

FIG. 4D is a perspective view of the abdominal support pad base;

FIG. 4E is a side view of the a support pad base;

FIG. 5 is a perspective view showing a user person seated on the abdominal support swivel chair of the present invention;

FIG. 6 is a simplified fragmented view illustrating the construction of the vertical and horizontal adjustment mechanism of the abdominal support pad; and FIG. 7 is a simplified view showing how these mechanisms are actuated.

MODES FOR CARRYING OUT THE INVENTION

Figure 2A:
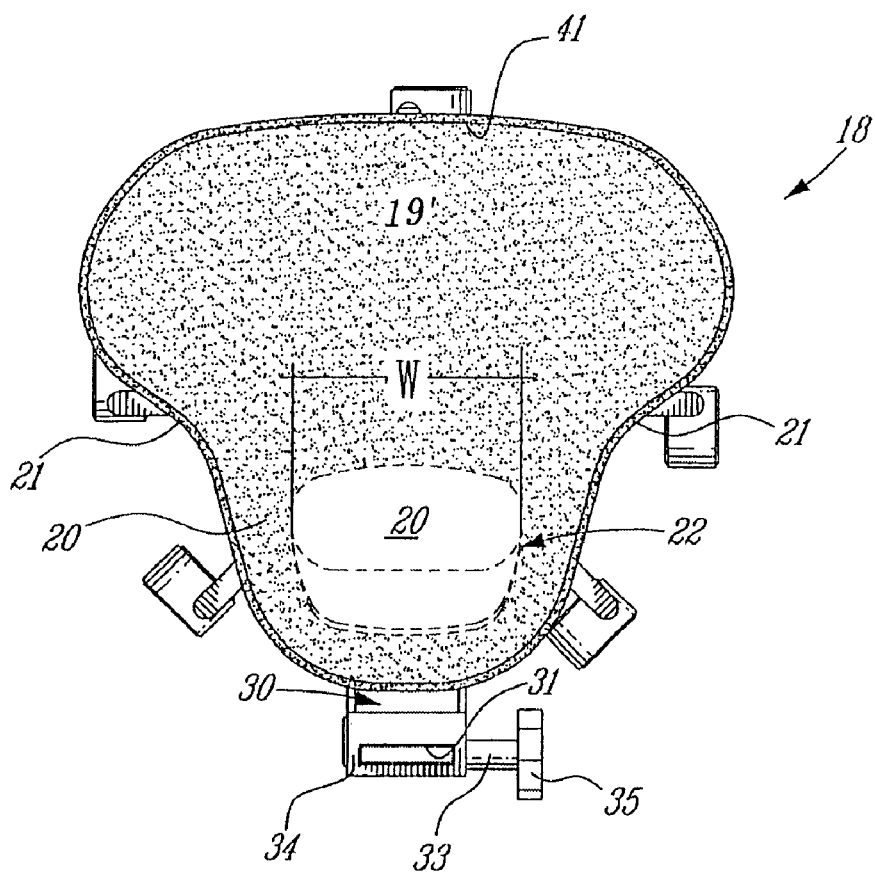
FIG. 2A is a top view of the saddle seat and showing the position of the securement member of the abdominal support pad adjustable support arm.

Referring now to the drawings and more particularly to FIG. 1, there is shown generally at 10 an embodiment of the abdominal support swivel chair constructed in accordance with the present invention. The chair comprises a base 11 having a central hub 12 from which a plurality of leg arms 13 radiate. The legs are all disposed in a horizontal plane and extend at a substantially common angle from the central hub 12, the angle 15 being about 45° or less, as illustrated in FIG. 3 of the drawings. Casters 16 are secured at the free ends of each of the leg arms.

The central hub 12 has an adjustable center post assembly 17 which extends vertically on a central longitudinal axis 14 from the center of the hub 12. A saddle seat 18 is secured to a saddle frame 19 which is connected at a top end of the center post assembly 17.

Figure 2B:
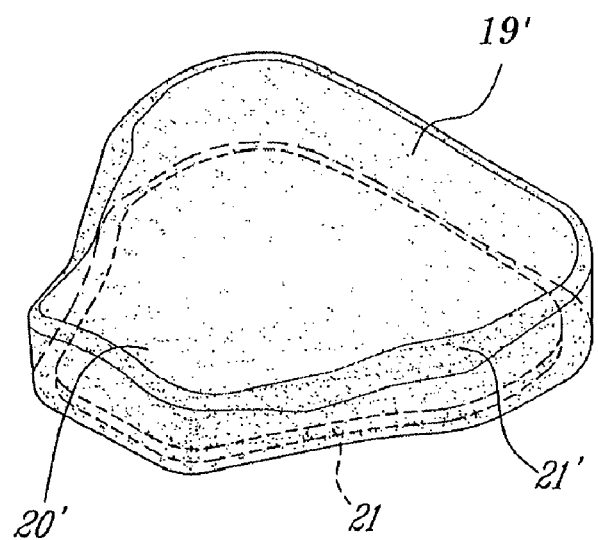
FIG. 2B is a perspective view of the saddle seat showing the shape of the upper support surface thereof.

As better seen in FIG. 2A, the saddle seat 18 has a large rear buttock support section 19' which is fairly wide to support the buttock area of a user person seated thereon. The buttock section 19' merges into a central narrow frontal projecting section 20 through opposed side thigh cavities 21. As hereinshown, the thigh side cavities define a concavely curved cavity whereby to provide comfort to the thighs of a person sitting on the saddle seat. As shown in FIG. 2B, the upper edge portion 21' depressed and rounded for comfort and to prevent hindrance to blood circulation in the legs of the user person at the thigh area. The frontal section 20 is also raised and defines a convex surface 20' and therefore is non-encumbering to a user person.

An abdominal support pad 22 is secured to an adjustable support arm 23 connected to the saddle frame 19. The support arm 23, as shown in FIGS. 4B and 4C, has an upper securing angled end section 24 which terminates in an angled attachment end section 24' which is adapted for securing the abdominal support pad 22 thereto. The adjustable support arm 23 is connected forwardly of the frontal projecting section 20 of the saddle seat and is centrally aligned therewith. Adjustable connecting means 30 is provided to position the abdominal support pad 22 at a desirable elevated position for the comfort of a user person. This adjustable connecting means 30 has adjustable means to permit the support pad to be inclined at an forward angle 25 which is about 20° to 25° from the vertical axis 14 of the base as shown in FIG. 4A.

As shown in FIGS. 1 and 4A, the adjustable connecting member 30 is secured at the front end of the saddle frame 19 and is provided with a vertical through bore 31, hereinshown as a vertical slot whereby to receive a lower straight section 32 of the adjustable support arm 23 therethrough. The adjustable support arm 23 is a flat metal bar or arm having a straight lower section 32 of a predetermined length whereby to provide vertical adjustment of the height of the abdominal support pad 22 relative to the saddle seat 18. This section 32 is received in the slot 31 and extends therethrough. An arresting means in the form of a threaded bolt 33 actuates a clamp 34 provided in the slot 31 to lock the support arm 23 at a desired position. A hand-operable knob 35 is secured to the free end of the bolt 33 to provide ease of rotation of the bolt to engage or disengage the straight lower section 32 of the adjustable support arm 23.

The adjustable support arm 23 is also shaped to define an inwardly and upwardly inclined section 36 above the straight section 32 which merges into a lower end of an intermediate, upwardly and slightly inwardly inclined section 37 and terminates in the attachment end section 24' which is disposed substantially parallel to the straight lower section 32. This recessed section 37 permits the user person sitting on the chair to work very close to a work environment as the section 37 is close to the body of the user person, as shown in FIG. 5.

The position of the abdominal support pad 22 relative to the saddle seat 18, is illustrated in phantom lines in FIG. 2, and it has a width W which is less than half the distance of a user's shoulders and at least one-third of that distance. The buttocks section 19 of the seat is approximately the maximum width of an average person's shoulders.

As shown in FIG. 3, another important feature of the chair is that the casters 16 are disposed along a circumferential axis 40 which lies about eight (8) inches from the central hub 12 and less encumbering to the feet of a user person. Also, the circumferential axis 40 lies substantially aligned with a rear edge 41 of the buttock support section 19 of the seat, as shown in phantom lines, and is disposed substantially under the securement member 30.

There is at least eight of these radiating leg arms and they define an angle 15 therebetween which is not greater than 45° whereby the chair will not overturn by the weight of a user person when displacing its body offset with respect to the center of gravity of the chair such as when leaning on one side of the chair to retrieve instruments or for any other reason. The closer spaced eight leg arms provide the stability to the chair.

As hereinshown, the vertical support post assembly 17 is secured about a connector 43 secured centrally of the base frame and the center post 9 has a lower connecting end which is received in a central sleeve 44 which connects into the connector 43 and about the central vertical axis 14. The seating saddle is free for axial rotation in the sleeve 44 whereby the saddle seat can be rotated along an arc of 360° about the base by the user person 26, see FIG. 5, seated on the seating saddle 18 and provides unobstructed access along this arc to the user person as this chair has no arm rests at the sides. The center post 9 is adjustably secured inside the sleeve by adjustment means, well known in the art, whereby to adjust the height of the seat with respect to a support surface on which the chair is displaced. A lever 44' provides for this adjustment and again this type of vertical adjustment for chairs is well known in the art.

As also shown in FIG. 1, the saddle seat 18 and the abdominal support pad 22 are provided with cushioning material to provide comfort to the user person.

Referring to FIGS. 4D and 4E there is shown the construction of the abdominal support pad base 75. The base 75 has a shape to provide comfort and freedom of movement to the user person. This base 75 has an inverted T-shape configuration defining opposed lower side wings 76 which have curved shaped outer edges 76'. The side wings are also inwardly curved, as shown in FIG. 4E towards the user person to conform to the roundish shape of the person's body. The side wings 76 also merge upwardly into a central vertical projecting arm 77 which has a slightly curved forward tilt, again to provide comfort when the user person bends forwardly against the support pad. The arm 77 has a curved free upper end. The shape of the base 75 and consequently the pad, as well as its size as previously describe are important to provide comfortable support and freedom of movement.

With reference now to FIGS. 4A, 6 and 7, there will be described an example of the construction of the vertically and horizontally adjustable mechanism for the abdominal support pad and a tilt mechanism for the saddle seat.

As previously described, the abdominal support pad 22 is adjustable vertically through the securement member 30 as previously described in the direction of arrows 48. This abdominal support pad 22 is also horizontally displaceable or tiltable in the direction of arrow 49 by means of a horizontal adjustment mechanism which will now be described with reference to FIGS. 6 and 7. The horizontal adjustment mechanism is comprised of a position adjusting linkage 50 connecting the securement member 30 to the saddle frame 19. As hereinshown, the securement member 30 is pivotally connected on pivot pin 51 to the saddle frame 19. The securement member 30 is also spring-biased by the coil spring member 52 for limited angular displacement with respect to the front end of the saddle frame 19. However, in order to angulate the adjustable support arm 23 at a desired angle to adjust the position of the abdominal support pad 22, there is provided a plurality of link plates 53 which are hingedly connected at one end to the securement member 30 about a connecting pin 54 and slidingly connected at an opposed end to a connecting pin 55 extending through a slot 56 of these link plates. As hereinshown the link plates 53 are spaced apart whereby to receive in close friction contact therebetween additional link plates 57 pivotally attached under the saddle seat 18 and having slots 57' through which the connecting pin 55 extends. The disposition of these plates is better illustrated in FIG. 7 and as can be seen these plates are urged in frictional engagement by a biasing spring 58 which is retained in a housing 59 urging the plates together under the force of the spring 58. An actuating mechanism 60 is actuated by a clutch arm 61 whereby to relieve the biasing force of the spring 58 whereby to disconnect the friction force from these plates and thereby permitting the securement member 30 to pivot on its pivotal pin 51 whereby to provide for the link plates 53 and 57 to reposition themselves with respect to the connecting pin 55 and providing adjustment, as indicated by arrow 49.

The connecting link plates 57 secured to the saddle seat 18 permit the saddle seat to be tilted along the direction of arrow 62 to pivot forwardly of axis 68 and downwardly or upwardly of axis 69, as illustrated in FIG. 4. The clutch or lever 61 is biased in a normally locked position by the pressure of the spring 58. When displaced to a first position, as indicated by reference numeral 61', the clutch disengages the biasing force against the link plates 53, permitting the securement member 20 and the adjustable support arm 23 to be moved along the directions of arrow 49. Upon further displacement of the clutch to the position as shown at 61", both the saddle seat and the abdominal support pad can be inclined or tilted simultaneously. Accordingly, the abdominal support swivel chair of the present invention can be adapted for the comfort of any user person.

FIG. 5 shows a user person 26 seated on the chair 10 and as can be seen the back of the person is inclined along the axis 70 while supported by the abdominal support pad 23 which relieves stress and pressure from the spinal cord of the user person. Also, the angle of the head of the user, illustrated by axis 71, is comfortably inclined due to the forward inclination of the saddle seat as well as the support pad 23, and this relieves tension on the neck of the user person thereby permitting the user person to be more comfortable and more productive in a day's work and substantially free of back or neck pains formerly caused by standard chairs having backrest supports and/or side arm supports. Because there are no side arms on the chair, and because of the shape and size of the abdominal support pad 23, the user's arms are free from movement from either side of the chair with the abdominal support pad 23 being non-obstructive to arm movements of the user person. If the user person needs to swing about the chair to retrieve instruments, etc., he can simply rotate the chair by using his feet on the floor or to displace the chair from side-to-side without having to step out of the chair. The short leg arms 13 also give him more feet movement about the chair. He can also bend his body from side-to-side without fear of the chair overturning which could be dangerous to the user person as well as the patient who is in close proximity to the user person, as illustrated in FIG. 5, wherein there is shown the position of a patient's chair 72, close to the user person, herein a dentist seated in a working position.

It is pointed out that the abdominal support pad and its support arm and adjusting mechanism can be secured to a variety of chairs adapted for various uses, such as a draftsman chair, where the user person needs to bend forwardly while effecting a work task.

It is within the ambit of the present invention to cover any obvious modifications of the preferred embodiment described herein, provided such modifications fall within the scope of the appended claims.

The invention claimed is:

1. An abdominal support swivel chair comprising a support base, disposable support means secured to said support base for displacing said chair on a support surface, an adjustable center post assembly extending vertically from a center of said support base along a central vertical axis of said support base, a saddle seat having a rear buttocks support section and a central narrow frontal projecting section merging therewith through opposed side thigh cavities, said saddle seat being secured to a seat frame connected at a top end of said adjustable center post, an abdominal support pad secured to an adjustable support arm connected to said seat frame forwardly of the central narrow frontal projecting section, the abdominal support pad comprising a support base of inverted T-shape configuration defining opposed lower side wings and a central vertical projecting arm having a forward outward tilt profile, said support arm having an upper securing end section adapted for securement of said abdominal support pad, said adjustable support arm being connected forwardly of said seat frame and aligned therewith, adjustable connecting means to position said abdominal support pad at a desired vertical position and a forwardly inclined position for the comfort of a user person, said adjustable connecting means comprises a vertical adjusting mechanism and a horizontal adjustment mechanism, said vertical adjusting mechanism having a securement member secured at a front end of said seat frame, a vertical through slot in said securement member, and arresting means for arresting engagement of said adjustable support arm in said through slot, said adjustable support arm being a flat metal bar, said through slot receiving a straight lower section of said flat metal bar therethrough, said flat metal bar also having an inwardly and upwardly inclined intermediate section above said straight lower section and merging into a lower end of an attachment end section disposed substantially parallel to said lower section and constituting said upper securing end section thereof, said arresting means having a threaded bolt portion for providing wedging engagement of a portion of said straight lower section extending in said through slot, and hand-operable means to engage and disengage said arresting means, said abdominal support pad being dimensioned to provide freedom of arm movement to a user person and supporting a central area of the abdomen of a user person, said horizontal adjusting mechanism comprising a pivot connecting the securement member to said seat frame such that the abdominal support pad is pivotable with respect to the seat frame, and biasing means related to the pivot to bias the abdominal support pad toward a substantially vertical position to oppose a force to a user leaning forwardly on the abdominal support pad when seated in the chair.

2. An abdominal support swivel chair as claimed in claim 1 wherein said support base is constituted by a plurality of leg arms radiating about said support base in a common horizontal plane from said center of said support base, said legs arms defining an angle of 45° or less therebetween, a caster secured at a free end of each said leg arms.

3. An abdominal support swivel chair as claimed in claim 2 wherein said casters are disposed along a circumferential axis which lies substantially aligned with a rear edge of said buttocks support section of said saddle seat and forwardly of said central narrow frontal projecting section thereof.

4. An abdominal support swivel chair as claimed in claim 3 wherein there are at least eight of said leg arms whereby said chair will not overturn by the weight of said user person when displaced off-set with respect to a center of gravity of said chair, said leg arms, defining between each of said arms an angle of about 45°.

5. An abdominal support swivel chair as claimed in claim 1 wherein said horizontal adjusting mechanism is comprised of a position adjusting linkage between said securement member and said seat frame, said securement member being pivotally connected to said seat frame, said securement member being spring-biased for limited angular displacement with respect to said seat frame, and hand-operable arresting means to engage and disengage said adjusting linkage to position said securement member and said support arm at a desired angle to effect horizontal adjustment of the position of said abdominal support pad.

6. An abdominal support swivel chair as claimed in claim 5 wherein said position adjusting linkage is coupled to a tilting mechanism whereby said seat can be tilted forwardly or rearwardly with respect to said abdominal support pad simultaneously with the tilting of said securement member.

7. An abdominal support swivel chair as claimed in claim 1 wherein said side wings have a curved outer side edge, said vertical projecting arm terminating in a rounded free end.

8. An abdominal support swivel chair as claimed in claim 7 wherein said center post has a connecting lower end received in a central hub disposed about said central vertical axis and free for axial rotation therein whereby said saddle seat can be rotated 360° about said base by said user person seated on said saddle seat, said support base providing unobstructed access about said chair.

9. An abdominal support swivel chair as claimed in claim 8 wherein said center post connecting lower end is adjustably secured to adjust the height of said saddle seat with respect to a support surface on which said chair is displaced.

10. An abdominal support swivel chair as claimed in claim 1 wherein said seat frame is secured to a tilting mechanism whereby said seat can be tilted forwardly towards said abdominal support pad for the comfort of said user person.

11. An abdominal support swivel chair as claimed in claim 1 wherein said inclined forward position contains an angle range of about 20° to 25° from said central vertical axis.

12. An abdominal support swivel chair as claimed in claim 1 wherein said abdominal support pad has a width which is less than half the distance of said user shoulder and at least one-third of said distance.

13. An abdominal support swivel chair as claimed in claim 1 wherein said center post has a connecting lower end received in a central hub disposed about said central vertical axis and free for axial rotation therein whereby said saddle seat can be rotated 360° about said base by said user person seated on said saddle seat, said support base providing unobstructed access about said chair.

14. An abdominal support swivel chair as claimed in claim 13 wherein said center post connecting lower end is adjustably secured to adjust the height of said saddle seat with respect to a support surface on which said chair is displaced.

15. An abdominal support swivel chair as claimed in claim 1 wherein said seat and said abdominal support pad are provided with a cushioned surface for comfort to said user person.

16. An abdominal support swivel chair as claimed in claim 1 wherein said opposed side thigh cavities are concavely curved cavities.

17. An abdominal support swivel chair comprising a support base, disposable support means secured to said support base for displacing said chair on a support surface, an adjustable center post assembly extending vertically from a center of said support base along a central vertical axis of said support base, a saddle seat having a rear buttocks support section and a central narrow frontal projecting section merging therewith through opposed side thigh. cavities, said saddle seat being secured to a seat frame connected at a top end of said adjustable center post, an abdominal support pad secured to an adjustable support arm connected to said seat frame forwardly of the central narrow frontal projecting section, said support arm having an upper securing end section adapted for securement of said abdominal support pad, said adjustable support arm being connected forwardly of said seat frame and aligned therewith, adjustable connecting means to position said abdominal support pad at a desired vertical position and a forwardly inclined position for the comfort of a user person, said adjustable connecting means comprises a vertical adjusting mechanism and a horizontal adjustment mechanism, said vertical adjusting mechanism having a securement member secured at a front end of said seat frame, a vertical through slot in said securement member, and arresting means for arresting engagement of said adjustable support arm in said through slot, said adjustable support arm being a flat metal bar, said through slot receiving a straight lower section of said flat metal bar therethrough, said flat metal bar also having an inwardly and upwardly inclined intermediate section above said straight lower section and merging into a lower end of an attachment end section disposed substantially parallel to said lower section and constituting said upper securing end section thereof, said arresting means having a threaded bolt portion for providing wedging engagement of a portion of said straight lower section extending in said through slot, and hand-operable means to engage and disengage said arresting means, said abdominal support pad being dimensioned to provide freedom of arm movement to a user person and, supporting, a central area of the abdomen of a user person, said horizontal adjusting mechanism comprising a pivot connecting the securement member to said seat frame such that the abdominal support pad is pivotable with respect to the seat frame, and biasing means related to the pivot to bias the abdominal support pad toward a substantially vertical position to oppose a force to a user leaning forwardly on the abdominal support pad, when seated in the chair, said support base being constituted by at least eight leg arms radiating from the center post assembly, a caster being secured at a free end of each said leg arm, whereby said chair will not overturn by the weight of said user person when displaced off-set with respect to a center of gravity of said chair, said leg arms defining between each of said arms an angle of about 45° or less.

18. An abdominal support swivel chair as claimed in claim 17 wherein said casters are disposed along a circumferential axis which lies substantially aligned with a rear edge of said buttocks support section of said saddle seat and forwardly of said central narrow frontal projecting section thereof.

* * * * *